United States Patent
Christ et al.

US 6,254,587 B1
Jul. 3, 2001

(54) METHOD FOR DELIVERING VISCOELASTIC MATERIAL TO AN EYE

(75) Inventors: F. Richard Christ, Laguna Beach; Edward R. Zaleski, Santa Ana, both of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/395,546

(22) Filed: Sep. 11, 1999

Related U.S. Application Data

(60) Division of application No. 08/832,460, filed on Apr. 2, 1997, now Pat. No. 5,984,889, which is a continuation-in-part of application No. 08/605,877, filed on Feb. 23, 1996, now abandoned.

(51) Int. Cl.[7] .................................................. A61M 31/00
(52) U.S. Cl. .............................. 604/521; 604/22; 604/294
(58) Field of Search ................................. 604/22, 48, 506, 604/521, 289, 290, 291, 294, 296, 297; 606/5, 6, 107, 41, 42, 169

(56) References Cited

U.S. PATENT DOCUMENTS

| | | | |
|---|---|---|---|
| 5,413,556 | * | 5/1995 | Whittingham .......................... 604/22 |
| 5,445,637 | * | 8/1995 | Bretton .................................. 604/22 |
| 5,746,713 | * | 5/1998 | Hood et al. ............................ 604/22 |

* cited by examiner

Primary Examiner—Manuel Mendez
(74) Attorney, Agent, or Firm—Walter A. Hackler

(57) ABSTRACT

A phacoemulsification handpiece for ophthalmic surgical procedures includes a needle having a tip and connected to a source of ultrasonic energy, for cutting and/or fragmenting eye tissue along with a conduit for introducing irrigation fluid proximate the needle tip. The handpiece also includes separate structure for introducing a viscous fluid, such as a viscoelastic material, proximate the needle tip as well as bore through the needle and handpiece for aspirating irrigation fluid, viscoelastic material end cut and/or fragmented eye tissue. An accumulator, connected to the housing is provided for containing a supply of viscous fluid. A diaphragm assembly and a manual valve are provided for delivering viscous material to the needle tip.

8 Claims, 2 Drawing Sheets

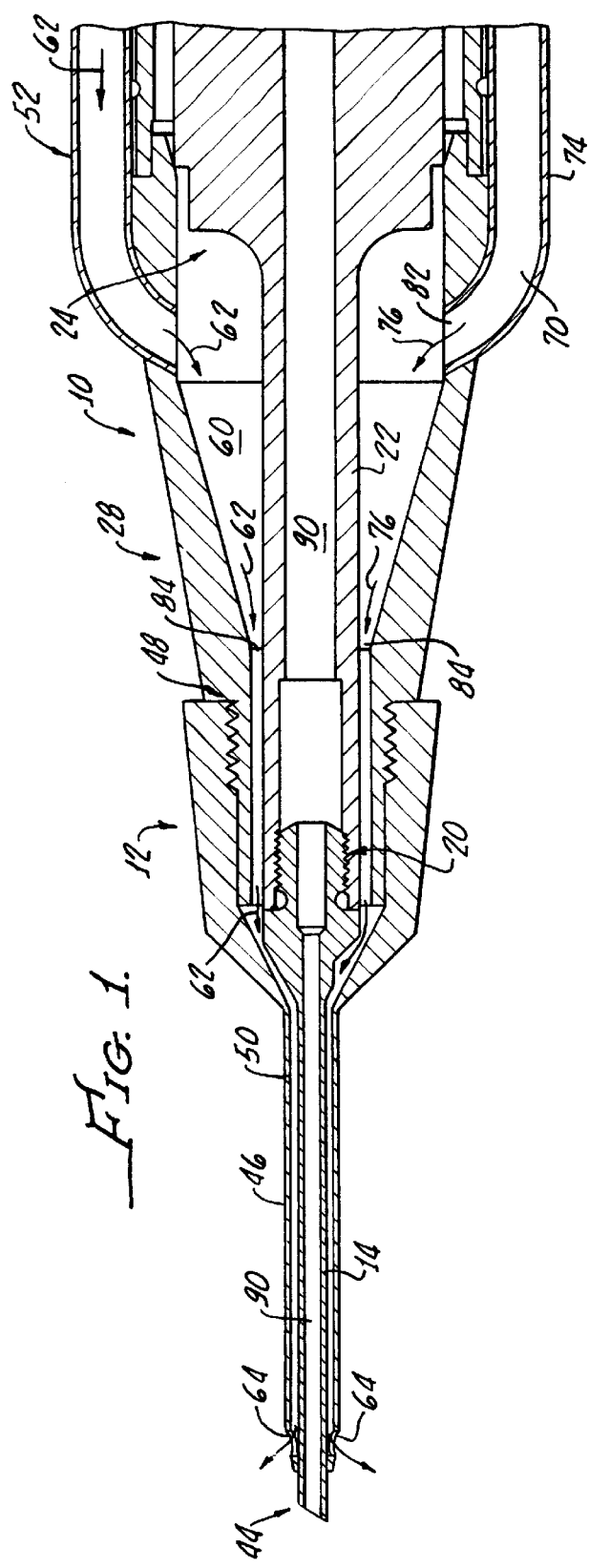
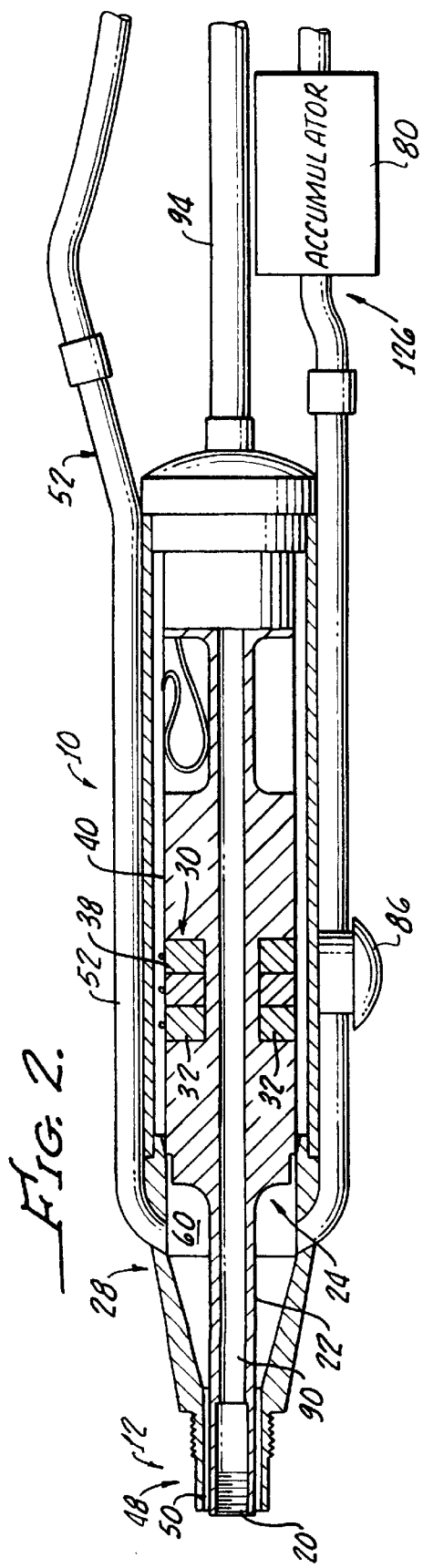
Fig. 1.
Fig. 2.

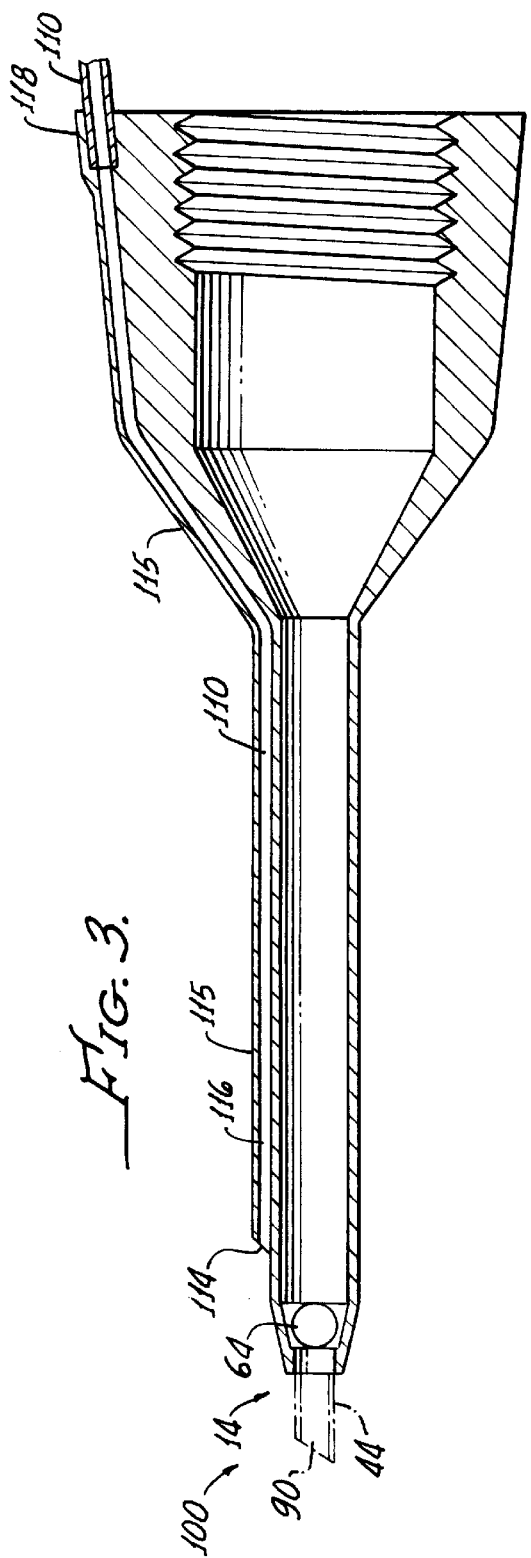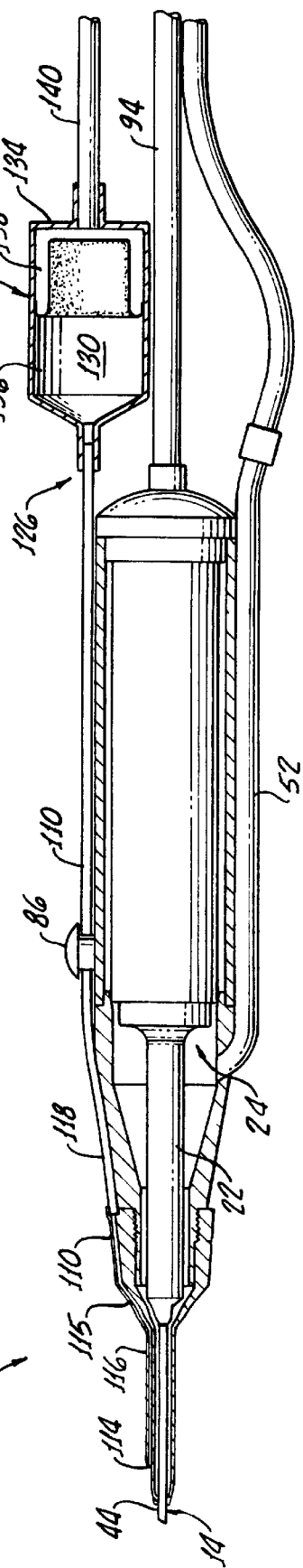

METHOD FOR DELIVERING VISCOELASTIC MATERIAL TO AN EYE

This is a divisional application of U.S. patent application Ser. No. 08/832,460, filed Apr. 2, 1997 now U.S. Pat. No. 5,984,889, which is a continuation in part of U.S. patent application Ser. No. 08/605,877, filed on Feb. 23, 1996, now abandoned.

The present invention generally relates to surgical instruments, and more particularly, is directed to a handpiece for ophthalmic surgical procedures. Phacoemulsification handpieces find common use by ophthalmic surgeons and are used for cutting, aspirating, and irrigating eye chambers during surgical operations. In view of the fact that ocular surgery many times includes the cutting and/or fragmenting of unwanted tissues, for example in cataract surgery, such cut or fragmented tissues must be removed from the eye.

Phacoemulsification involves the generation of an ultrasound signal which is a series of cyclical mechanical vibrations in a frequency range beyond that detectable by normal human hearing. The ultrasonic signal is generated by a transducer that is driven by an electrical signal in the frequency range between about 20 and about 100 kHz in equipment presently available for this application. Typically the transducer mechanism includes either piezoelectric or magnetostrictive elements.

The energy resulting from the ultrasonic signal is coupled to the human lens by a needle attached to the transducer. Typically, the needle is made from an inert alloy of titanium or stainless steel. Once coupled to the human lens, the ultrasonic energy is capable of cutting, fragmenting and emulsifying tissue, for example a cataract. Once the material is fragmented, however, it must be removed from the eye. In order to accomplish the removal of unwanted tissue particles, the ultrasonic needle and is hollow and an aspiration system is connected to the hollow needle. A balanced saline solution is typically injected into the eye during the surgical procedure in order to irrigate the tissue and facilitate aspiration of the tissue particles. The saline solution is infused into the surgical site by means of a hollow sleeve surrounding the needle.

Thus, a single phacoemulsification handpiece not only provides a device for cutting and/or fragmenting eye tissue but for providing irrigating fluid and the subsequent aspiration of the fluid and cut or fragmented tissue.

Importantly, in many ophthalmic surgical procedures such as, for example, in ocular lens implantation, cataract surgery, and retinal detachment repair, a viscous gel-like composition is also injected into the eye at some time during the surgical procedure. The viscous gel-like composition is used to coat the chambers of the eye in order to protect sensitive tissue in particular, the corneal and endothelium, from trauma.

These gel-like materials are generally classified as viscoelastic materials. While many compositions have been utilized, commonly employed compositions include solutions of hyaluronic acid, chondroitin sulfate and methylcellulose. The many various viscoelastic materials are generally termed as either adhesive viscoelastic, such as Viscoat®, or cohesive viscoelastic, such as Healon®.

Accordingly, as will be surmised from the hereinabove noted ophthalmic surgical procedures, the phacoemulsification handpieces for fragmentation, irrigation and aspiration, are commonly used with additional and distinct apparatus suitable for introducing and/or a removal of such viscoelastic material. A brief description of the types of viscoelastic material utilized and methods utilized is given in U.S. Pat. No. 5,358,473 which is herewith incorporated by reference in order to provide disclosure for the types of viscoelastic materials and the procedures commonly utilized in ophthalmic surgeries employing such viscoelastic materials.

Adhesive and cohesive viscoelastic materials have the characteristic of becoming more viscous upon application of pressure thereon.

Conventionally, this material is injected into the eye chambers by means of a hand held syringe or cannula. Because the flow characteristics and viscosity of viscoelastic materials vary to some degree depending upon such factors as the particular composition of the material, the temperature of the material, and the overall geometry of the injection apparatus, a manually operated syringe is commonly used to enable direct physician control of the injection rate of the material into the eye. In addition, the manual syringe provides for injection of the material through a short lumen, which is important in light of the property of the material becoming more viscous upon an increase in external pressure.

Viscoelastic material is injected into the eye at the beginning of the surgical procedure and oftentimes during the procedure in the event a physician determines that additional protection of sensitive eye tissue is required.

Thus, it is conventional for a physician to switch instruments during surgery in order to perform these various important tasks.

Because multiple tasks are attended to during intraocular surgery which must be carefully and precisely performed, it would be clearly advantageous to enable a physician to perform such multiple tasks using a single hand held, easily controllable instrument rather than using multiple instruments for different tasks. In addition, it would be advantageous to enable the performance of intraocular surgery through a single incision in the eye.

It should be appreciated that frequent switching of surgical instruments during delicate eye surgery presents increased risk of injury and infection to the patient.

The present invention provides for such an instrument, particularly a phacoemulsification handpiece which represents a unique combination of heretofore separate instruments. The present invention provides for an improved handpiece which facilitates and enhances a surgeon's ability to conduct a multitude of ophthalmic surgical procedures through a single incision and without switching instruments.

SUMMARY OF THE INVENTION

A phacoemulsification handpiece in accordance with the present invention for ophthalmic surgical procedures generally includes a housing, a horn, a transducer disposed in the horn and providing means for generating ultrasonic energy, and a needle, coupled to the horn and providing means for radiating the ultrasonic energy into an eye for fragmenting and/or cutting eye tissue in a conventional fashion, said needle including an tip. In addition, the handpiece of the present invention includes means for delivering an irrigation fluid into the eye and proximate the needle tip during the surgical procedure.

Importantly, the handpiece also includes delivery means, such as a conduit, for delivering a viscous fluid to the eye and proximate the needle tip. The conduit may comprise structure, defining a lumen, disposed longitudinally along the needle and having an outlet for the viscoelastic material proximate the needle tip. Alternatively, the conduit may be integrated into the irrigation fluid pathway such that the two fluids may be combined prior to dispensing thereof.

Thus, the viscous fluid and irrigation fluid may be separately dispensed by means of separate fluid pathways. In other words, in one embodiment of the present of the invention, structure is provided for introducing the viscous material proximate the needle separately from the eye irrigation fluid. This should be contrasted with the first embodiment in which the irrigation fluid and the viscous material may be commingled before introduction approximate the needle.

In conjunction with the delivery means, an accumulator provides means for containing a supply of viscous fluid to be dispensed at the surgical site. Preferably, because of the high viscosity of the material which must flow through the means for delivering same, the accumulator means is disposed a short distance from an outlet for the viscoelastic material. The accumulator means is preferably disposable and removably connected to the housing.

The accumulator preferably includes means for dispensing said viscous fluid upon demand to the delivery means. This feature includes, in part, a flexible diaphragm defining a first chamber filled with viscous fluid and a second chamber filled with pressurized air. The second chamber may be connected to a phacoemulsification machine adapted for providing a constant, controlled source of air pressure. In addition, the means for dispensing the viscous fluid preferably includes a normally closed valve disposed on the housing, said valve enabling manually controlled dispensing of the viscous fluid.

Additionally, the handpiece includes aspiration means for removing irrigation fluid, viscous fluid and tissue fragments from the eye. Said aspiration means may comprise a hollow portion of said horn in fluid communication with a bore through said needle means. As is conventional, the aspiration means may be connected to a vacuum source in the phacoemulsification machine.

Preferably, the viscous material being introduced comprises a viscoelastic material such any one of a variety of viscoelastic materials often utilized during ophthalmic surgery, for protecting the eye. It should be appreciated that while the hereinafter presented discussion is specifically directed to the introduction of a viscoelastic material, other fluid materials, which may be desirable to introduce into the eye during phacoemulsification, are to be considered within the scope of the present invention.

Hence, the handpiece of the present invention provides a single instrument which can perform multiple functions, including the function of enabling injection of viscoelastic material.

In accordance with the apparatus of the present invention, only one phacoemulsification handpiece is necessary in order to cut, irrigate, aspirate eye tissue as well as provide and remove viscoelastic material as may be necessary.

BRIEF DESCRIPTION OF THE DRAWINGS

The advantages and features of the present invention will appear from the following description, when considered in conjunction with the accompanying drawings in which:

FIG. 1 is a cross-sectional view of a tip portion of a phacoemulsification handpiece, including a phacoemulsification needle, in accordance with the present invention;

FIG. 2 is a side view of the phacoemulsification handpiece shown in FIG. 1, partially broken away, showing conduits for delivery of an irrigation fluid and a viscous fluid to a surgical site, the handpiece shown having the needle shown in FIG. 1 removed for the sake of clarity;

FIG. 3 is a cross-sectional view of another embodiment in accordance with the present invention showing a portion of the phacoemulsification handpiece having a conduit comprising lumen structure for enabling separate delivery of said viscoelastic material to the needle tip;

FIG. 4 is a cross-section of a side view of the phacoemulsification handpiece for which the needle portion is shown in FIG. 3.

DETAILED DESCRIPTION

Turning now to FIGS. 1 and 2, an embodiment of a phacoemulsification handpiece 10, in accordance with the present invention, is shown. For the sake of simplicity, FIG. 1 generally shows a tip portion 12 of the handpiece including a needle 14 threadably enagaging at 20 a stem portion 22 of a horn 24, and FIG. 2 generally shows the handpiece 10 with the needle 14 removed therefrom.

More particularly, the handpiece 10 includes a housing 28, and the horn 24 is disposed therein. An ultrasonic transducer 30, such as piezoelectric crystals 32 disposed in the horn 24, is provided for generating ultrasonic energy.

It should be appreciated that the horn 24 and piezoelectric crystals 32 may be of any conventional suitable design heretofore used in phacoemulsification handpieces. The housing 28 and horn 24 may be formed from any suitable material such as titanium or stainless steel.

Electrical connection to the piezoelectric crystals 32 may be made through terminals 38 connected by a wire 40 which is ultimately connected to a power source (not shown). An electrical signal, in the ultrasonic frequency range of for example between about 20 kHz and about 100 kHz is transmitted to the transducer 30 from the power source.

It should be appreciated that the handpiece of the present invention is generally utilized in conjunction with a conventional phacoemulsification machine (not shown).

Similar to conventional phacoemulsification handpieces, the needle 14 includes a tip 42, which upon vibrating at ultrasonic frequencies, is capable of cutting or fragmenting eye tissue. Thus, the needle 14 provides means for radiating ultrasonic energy into an eye in order to cut, fragment or emulsify tissue, depending upon the particular surgical procedure being conducted.

In addition, as most clearly shown in FIG. 1, a sleeve 46 surrounds most of the needle 14 and includes a threaded engagement with the handpiece housing 28 at 48. The sleeve 46 may be disposable or autoclavable.

The sleeve 46 defines a conduit 50 surrounding the needle 14 and provides means for delivering an irrigation fluid into the eye and proximate the needle tip 44.

An irrigation tube 52 connected to a source or irrigation fluid (not shown), may be integrated into the housing and/or disposed exterior thereto. The irrigation tube 52 functions to dispense irrigation fluid into a hollow chamber 60 in said housing 28 which is in fluid communication with the sleeve conduit 50.

The irrigation tube 52, chamber 60 and sleeve 46 thus establish an irrigation pathway, or irrigation conduit for fluid flow in a direction represented by arrows 62 in FIG. 1, and which reaches the surgical site through outlets 64.

Importantly, in addition to the delivery of irrigation fluid, the present invention includes means for delivering a viscous fluid to the eye and proximate the needle tip 44. More particularly, the means for delivering a viscous fluid includes, in part, a conduit 70, having an outlet 72 adjacent the needle tip 44. The viscous fluid conduit 70 may be include a line 74 integrated into the housing 28 or secured exterior thereto. The line 74 may dispense viscous fluid into the housing chamber 60, which will hereinafter sometimes be referred to as a "mixing chamber" for reasons that will become clear. The mixing chamber 60 provides means for combining the viscous fluid with irrigation fluid prior to dispensing of a mixture thereof. In other words, the viscous fluid conduit will, in the embodiment shown in FIGS. 1 and 2, be integrated with the irrigation conduit downstream of the mixing chamber 60.

Mixing of the fluids occurs in the mixing chamber 60 due to a restriction of flow occurring downstream of the chamber as shown at 84 in FIG. 1.

A valve 86 is provided for enabling simultaneous dispensing of irrigation fluid and a desired amount of viscoelastic material into the chamber 60.

The present invention further comprises aspiration means for removing irrigation fluid, viscous fluid and tissue fragments from the eye. More particularly, the needle 14 and horn 24 may include a bore 90 therethrough, said bore being connected to an aspiration tube 94 to which a vacuum is applied in a conventional manner by the phacoemulsification machine, again, being of any suitable design and not part of the present invention.

Turning now to FIGS. 3 and 4, an alternative embodiment 100 of the present invention is shown in which common character references refer to identical or substantially similar structural elements common to both embodiments 10, 100.

For the sake of clarity, FIG. 3 generally shows a portion of the present invention with the needle 14 removed therefrom, although a portion of the needle tip 44, as if the needle 14 was not removed, is shown in phantom line.

In this embodiment 100, the viscoelastic material is not mixed or combined with the irrigation fluid prior to dispensing thereof from the handpiece 100. More particularly, the viscoelastic material is introduced by means of a separate viscous fluid conduit 110 disposed longitudinally along the needle 14 and having an outlet 114 adjacent the needle tip 44. More particularly, the viscous fluid conduit 110 may be defined in part, by structure 115 defining a lumen 116 on the sleeve 46, and by suitable, complementary, engaging structure 118 on the housing 28.

Thus, as shown in FIG. 3, irrigation fluid is introduced to the eye through outlet 64 and viscous fluid is introduced through distinct outlet 114, both being proximate the needle tip 44.

Importantly, the viscous fluid conduit, in either embodiment hereinabove described, 70, 110 is connected, by suitable fittings 126 to the accumulator 80 briefly described hereinabove, which will now be described in greater detail.

Preferably, the accumulator 80 includes means for dispensing the viscoelastic material, on demand, to the delivery means. For example, referring now to FIG. 4, viscoelastic material 130 contained in the accumulator 80, my be subjected to a constant source of pressure, and the valve 86 may be normally closed so that upon a physician manually opening the valve 86, the viscoelastic material 130 will be released into the conduit 110 and injected from outlet 114 into the surgical site. Of course, it should be appreciated that in the first embodiment, the viscoelastic material may first be combined with irrigation fluid in the mixing chamber 60.

The valve 86 may thus comprise any suitable mechanism that will open a flow of the viscoelastic material 130 under pressure, upon manual activation thereof and further which will positively, automatically close the flow of material upon manual release thereof. This may be compared to conventional apparatus for injecting viscoelastic material, which is typically a syringe having a finger operated plunger in which the physician must manually control the pressure required to release the appropriate amount of material into the eye while holding the syringe steady with the same hand.

The diaphragm 134 which may be made of any suitable material, for example silicone, may define a first chamber 136 and a second chamber 138. The first chamber 136 is used for containing a selected amount of the viscous fluid 130 and the second chamber 138 is air filled and connected to a source of air pressure by means of suitable tubing 140, or the like, to the phacoemulsification machine.

Constant pressure supplied to the accumulator 80 may be provided by a solenoid pump (not shown) integrated into the phacoemulsification machine. Alternatively, air pressure may be supplied by a vitrectomy air compressor, such air compressors being well known in the art.

In operation, the viscoelastic material 130 is forced from the first chamber 136 through the conduit 110 and from the outlet 114 by means of the diaphragm 134 pressing the material 130 due to the air pressure supplied through tubing 140, and manual release of the valve 86.

It should be appreciated that instead of the diaphragm assembly hereinabove described, the means for dispensing the viscous fluid on demand may be a piston and spring assembly or other suitable mechanism.

In order to provide a compact, easily handled handpiece, the accumulator may be integrated into the housing while also being removable therefrom for purposes of filling with viscoelastic material or replacement. The accumulator may be made of easily assembled components and inexpensive materials such that it may be entirely disposable.

It should be appreciated that a method in accordance with the present invention utilizes the herein described phacoemulsification handpiece and includes in one instance the mixing in a single phacoemulsification handpiece, irrigation fluid and viscoelastic material to form a mixture, introducing the mixture proximate the emulsification needle during eye surgery, and thereafter, aspirating the mixture and the lens tissue.

In addition, the present invention may also include the steps of making a single incision in an eye and introducing a phacoemulsification needle into the incision for cutting and/or fragmenting eye tissue using a phacoemulsification handpiece. An irrigation fluid is introduced proximate the needle within an eye chamber with the same phacoemulsification handpiece.

Importantly, also introduced by the same phacoemulsification handpiece and into the same single incision is a viscoelastic material.

The irrigation fluid and viscoelastic material may be mixed prior to the dispensing of the fluids in the eye or they may be introduced separately.

Advantageously the needle need not be removed from the incision during fragmenting or emulsifying and during the introduction of the fluids because there is no need for switching surgical instruments.

Finally, the method includes utilizing the same phacoemulsification handpiece to aspirate the cut and/or fragmented eye tissue, irrigation fluid, and the viscoelastic material from the eye chamber.

Again, the method of the present invention enables irrigation of the surgical site, as well as introduction of viscoelastic material and aspiration of tissue and fluids without the need to remove the needle from the site and without the need to change instruments. The apparatus and method of the present invention thus reduces chance of infection and enhances safety of ophthalmic surgery.

Although there has been hereinabove described a specific arrangement of a phacoemulsification handpiece and method for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method useful in ophthalmic surgical procedures, the method comprising the steps of:

radiating ultrasonic energy from a needle tip of a phacoemulsification handpiece, into an eye in order to cut, fragment or emulsify eye tissue;

delivering an irrigation fluid to the needle tip;

delivering a viscoelastic material to the needle tip;

mixing the irrigation fluid and viscoelastic material inside the phacoemulsification handpiece prior to the steps of delivering the irrigation fluid and viscous material;

aspirating cut, fragmented or emulsified eye tissue, irrigation fluid and viscous fluid from the eye, the steps of delivering an irrigation fluid, delivering a viscoelastic material and aspirating, performed without removing the needle from the eye.

2. The method according to claim 1 further comprising the step of making a single incision in the eye with the needle tip, and wherein the steps of radiating ultrasonic energy, delivering irrigation fluid, delivering viscoelastic material and aspirating are performed through the single incision.

3. An ophthalmic surgical procedure comprising the steps of:

fragmenting eye tissue using an ultrasonically driven needle tip;

simultaneously delivering a viscoelastic material to the eye proximate the needle tip, the delivery including mixing the viscoelastic material with the irrigation fluid before delivering to the eye, the mixing occurring in a chamber within a handpiece supporting the needle tip; and aspirating irrigation fluid, viscoelastic material and tissue fragments from the eye.

4. The procedure according to claim 3 further comprising the step of accumulating the viscoelastic material in a handpiece accumulator prior to mixing same with irrigation fluid in the handpiece chamber.

5. The procedure according to claim 4 further comprising supplying the viscoelastic material to the handpiece accumulator and chamber by compressed air.

6. An ophthalmic surgical procedure comprising the steps of:

fragmenting eye tissue;

delivering an irrigation fluid into the eye proximate the fragmented eye tissue;

simultaneously delivering a viscelastic material to the eye proximate the fragmented eye tissue, the delivery including mixing the viscoelastic material with the irrigation fluid before delivering the eye, the mixing occurring in a chamber within a handpiece apparatus for fragmenting the eye tissue; and aspirating irrigation fluid, viscoelastic material and tissue fragments from the eye.

7. The procedure according to claim 6 further comprising the step of accumulating the viscoelastic material in a handpiece accumulator prior to mixing same with irrigation fluid in the handpiece chamber.

8. The procedure according to claim 7 further comprising supplying the viscoelastic material to the handpiece accumulator chamber by compressed air.

* * * * *